United States Patent
Voser et al.

(10) Patent No.: US 9,612,206 B2
(45) Date of Patent: Apr. 4, 2017

(54) CASH VALIDATOR AND METHOD FOR DETECTING TAPE ON A DOCUMENT

(71) Applicant: MEI, Inc., Malvern, PA (US)

(72) Inventors: Christian Voser, Vessy (CH); Sebastien Menot, Thoiry (FR)

(73) Assignee: CRANE PAYMENT INNOVATIONS, INC., Malvern, PA (US)

( * ) Notice: Subject to any disclaimer, the term of this patent is extended or adjusted under 35 U.S.C. 154(b) by 552 days.

(21) Appl. No.: 14/033,740

(22) Filed: Sep. 23, 2013

(65) Prior Publication Data

US 2014/0084189 A1    Mar. 27, 2014

(30) Foreign Application Priority Data

Sep. 26, 2012   (EP) ..................................... 12186151

(51) Int. Cl.

| | |
|---|---|
| *G01N 21/88* | (2006.01) |
| *G07D 7/20* | (2016.01) |
| *G01N 21/956* | (2006.01) |
| *G07D 7/12* | (2016.01) |
| *G01N 21/84* | (2006.01) |
| *G07D 7/18* | (2006.01) |

(52) U.S. Cl.
CPC ............. *G01N 21/88* (2013.01); *G01N 21/84* (2013.01); *G01N 21/956* (2013.01); *G07D 7/121* (2013.01); *G07D 7/185* (2013.01); *G07D 7/187* (2013.01); *G07D 7/20* (2013.01)

(58) Field of Classification Search
CPC ...... G07D 7/121; G07D 7/185; G07D 7/2025; G07D 7/122; G07D 7/00; G07D 7/20; G07D 7/187; G01B 11/00; G01N 21/94; G01N 21/956; G01N 21/84; G01N 21/88
USPC ...... 250/559.41, 221, 559.01, 559.4, 559.45, 250/222.1, 222.2, 239
See application file for complete search history.

(56) References Cited

U.S. PATENT DOCUMENTS

| | | | | |
|---|---|---|---|---|
| 4,617,080 A | * | 10/1986 | Kobayashi | .......... B32B 38/1841 156/359 |
| 5,790,697 A | * | 8/1998 | Munro | ................... B65H 3/063 209/546 |
| 6,062,369 A | * | 5/2000 | Negishi | .................... B65H 7/14 194/207 |

(Continued)

FOREIGN PATENT DOCUMENTS

| | | | | |
|---|---|---|---|---|
| JP | 10275406 A | * | 10/1998 | |
| JP | 11045362 A | * | 2/1999 | |
| KR | WO 03063096 A1 | * | 7/2003 | ............... G07D 7/18 |

*Primary Examiner* — Que T Le
*Assistant Examiner* — Jennifer Bennett

(57) ABSTRACT

A device and a system for detecting a tape or a piece of glue on a document and methods for detecting a tape or a piece of glue on a document are described. The device comprises at least one light source, at least one light receiver and at least one light barrier. The at least one light source is arranged on a first side of the at least one light barrier and the at least one light receiver is arranged on a second side of the at least one light barrier opposite to the first side. The light barrier is configured to come into contact with a document to prevent or reduce light emitted from the light source on the first side of the light barrier to be transmitted to the light receiver on the second side of the light barrier.

23 Claims, 8 Drawing Sheets

(56) References Cited

U.S. PATENT DOCUMENTS

| | | | |
|---|---|---|---|
| 7,018,121 B2 * | 3/2006 | Barry | B41J 11/009 |
| | | | 250/239 |
| 7,182,197 B2 * | 2/2007 | Nago | G07D 7/122 |
| | | | 194/207 |
| 2006/0214362 A1 * | 9/2006 | Matsumoto | B65H 29/12 |
| | | | 271/225 |
| 2011/0052082 A1 * | 3/2011 | Parkov | G06K 9/2018 |
| | | | 382/209 |

* cited by examiner

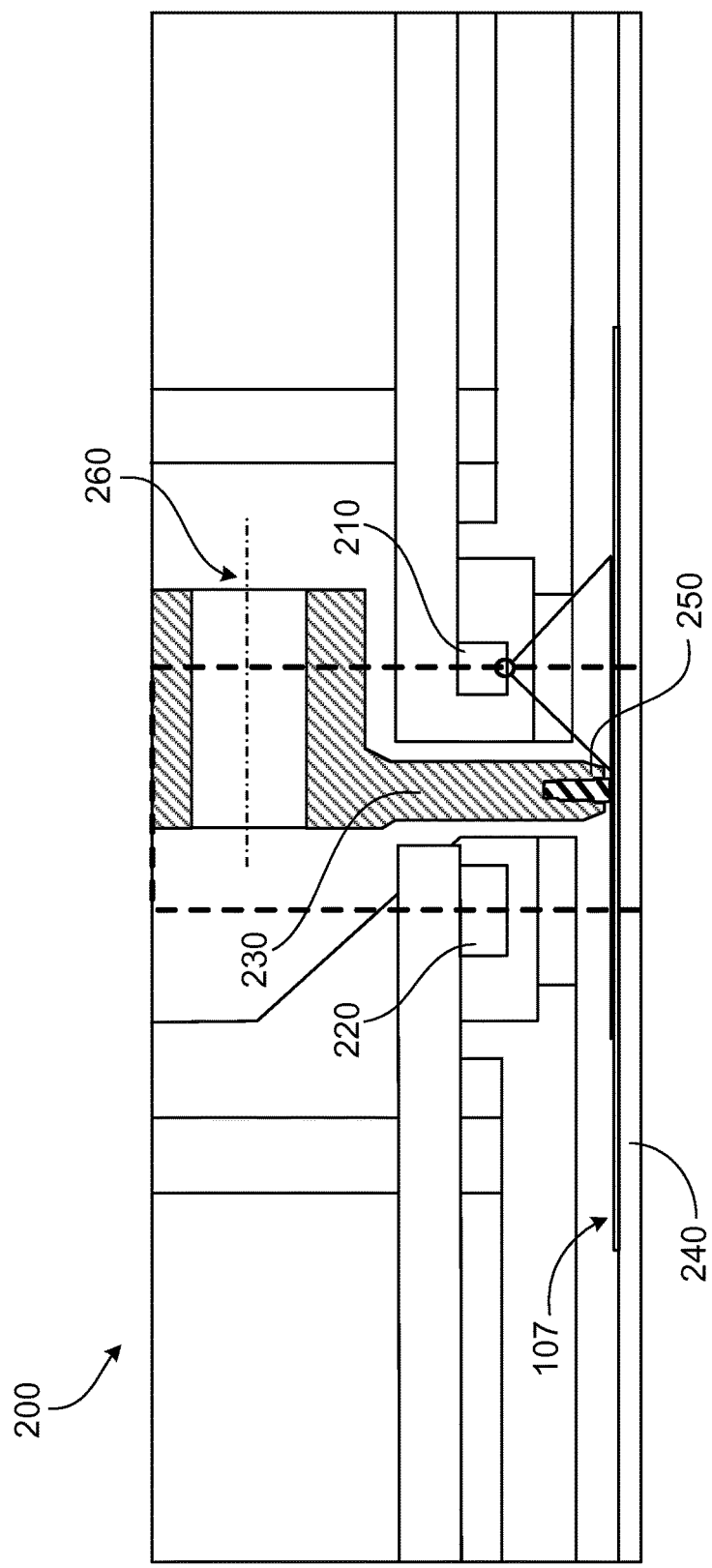

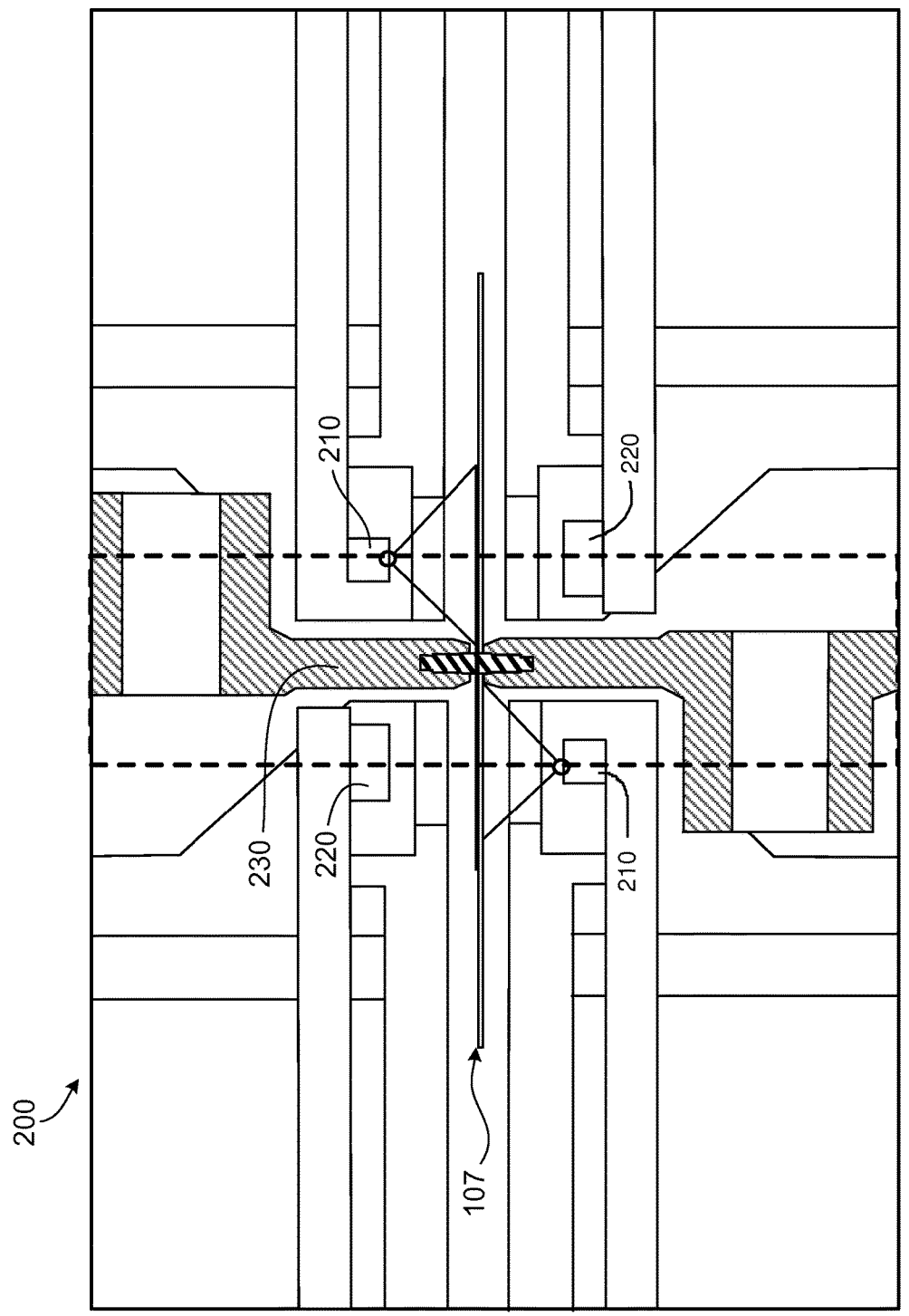

CASH VALIDATOR AND METHOD FOR DETECTING TAPE ON A DOCUMENT

RELATED APPLICATIONS

This application claims priority to European Patent Application No. 12 186 151.2, filed Sep. 26, 2012, the contents of which are hereby incorporated by reference.

FIELD OF DISCLOSURE

This disclosure relates to a device and a system for detecting a tape on a document and methods for detecting a tape on a document. For the purpose of this disclosure, the term document includes, but is not limited, to a banknote, sheet, bill, coupon, security paper, currency, ticket, or any other flexible planar item of the same nature.

BACKGROUND

Documents of any kind are used to pay for goods. A rising number of goods, e.g. food, toys, medicine, tickets, and so forth are available at vending machines. The customer can pay at these vending machines or at automatic cash out devices with documents, e.g. bills, banknotes or coupons. The machines accepting the documents for a transaction have to provide a high reliability when validating the documents. There are several reasons why inserted documents are not acceptable. In case the documents are not acceptable, the machines should reject the documents back to the user to avoid financial loss for the company operating the machines. For example, the documents could be counterfeits and therefore not acceptable. Further, the documents could be damaged or torn. Customers using vending machines may try to fix damaged or torn documents. Often glue or tapes, in particular transparent tapes, may be used to fix the damaged or torn documents. These fixed documents might have less or no value for the company operating the machines. The tapes used for fixing the documents can be very thin (40-50 μm) and the tape pieces can be as small as 5 by 15 mm or even smaller. These factors may be considered when developing devices and systems for document accepting machines that are capable of detecting any kind of tapes, in particular transparent tapes, applied to a valuable document. A device for detecting such tapes on documents can avoid the acceptance of damaged or torn documents. Such devices can be included into document accepting machines. Therefore, these devices should have a compact design and a high reliability.

SUMMARY

The present subject matter can relate to a device for detecting a tape on a document according to claim 1. Further, the present subject matter relates to a system according to claim 10, a cash validator according to claim 13, a vending machine according to claim 14 and a method for detecting a tape on a document according to claim 15.

The term tape as used in the present application is not limited to a strip or piece of tape but can also be a thin layer of glue or adhesive used to repair a document.

In an aspect, the device for detecting a tape on a document of the present subject matter can comprise at least one light source, at least one light receiver, and at least one light barrier. The at least one light source can be arranged on a first side of the at least one light barrier, the at least one light receiver can be arranged on a second side of the at least one light barrier opposite to the first side. The light barrier can be configured to come into contact with a document to prevent or reduce light emitted from the light source on the first side of the light barrier to be transmitted to the light receiver on the second side of the light barrier. The light source, the light barrier, and the light detector of the device can be located on the same side of the document.

According to another aspect of the present subject matter, the device can be arranged so that when a piece of tape is attached to a region of the document where the light barrier is in contact with the document, an amount of light is transmitted from the light source through the piece of tape to the light receiver on the other side of the light barrier. A light intensity detected by the light receiver when a piece of tape is attached to a region of the document where the light barrier is in contact with the document can be at least 2 times, in particular at least 5 times higher than a light intensity detected when the document does not have a piece of tape attached to the region of the document where the light barrier is in contact with the document. The light intensity detected when a piece of tape is attached to the document can be between 2 and 100 times, between 5 and 50 to times, in particular between 10 and 25 times higher than the light intensity detected without a tape on the document. The piece of tape can have a thickness between 10 μm to 200 μm, in particular between 20 μm and 100 μm, in particular between 30 μm and 60 μm. The dimensions of the piece of tape that can be detected by the device can be between 15 mm by 80 mm and 5 mm by 10 mm.

The device can further comprise a document transport path and a transport means to forward the document along the transport path. The document transport path and the light barrier can be arranged so that the document is forwarded along the document transport path by the transport means and can come into contact with the light barrier when passing the light barrier.

According to another aspect, a plurality of light barriers can be arranged across a width of a detection region and/or across a length of the detection region. The distance between respective of the plurality of light barriers can be between 2 mm and 15 mm, in particular between 4 mm and 8 mm, in particular between 5 mm and 7 mm. A plurality of light sources and a plurality of light receivers can be arranged between the plurality of light barriers. The plurality of light barriers can be arranged to build at least three compartments and one or more of either the plurality of light sources or the plurality of light receivers can be arranged per compartment. The light sources and the light receivers can be arranged alternately in consecutive compartments. In particular, when one or more light sources are arranged in a first compartment then one or more light receivers are arranged in compartments adjacent to the first compartment or when one or more light receivers are arranged in the first compartment, one or more light sources are arranged in the compartments adjacent to the first compartment. Thus, the device can have compartments having alternatively light sources or light receivers and there are no compartments next to each other on the same side of the document that have both a light source or both a light receiver. This can be advantageous, for example, and in no way limiting the scope or interpretation of the claims, because the light from one light source can be detected by all the light receivers arranged in the compartments adjacent to the compartment with the light source. Hence, in the non-limiting example, a compact and efficient arrangement can be realized.

According to another aspect, at least a portion of the one or more light barriers comprises a deformable material; in particular, a portion coming into contact with the document comprises the deformable material. A remaining portion of the one or more light barriers can comprise a different material with a higher module of elasticity than the portion coming into contact with the document. Alternatively or additional, one or more counter components, arranged on the opposite side of the document, can comprise a deformable material contacting the document on a side of the document that is opposite to the side of the document where the light barrier is in contact with the document. The deformable material can be applied to either the one or more light barriers or the one or more counter components. The deformable material can also be applied to both, the one or more light barriers and the one or more counter components. The deformable material can thus be in contact with the document on either both sides of the document, or the deformable material can be in contact with the document on one side of the document and a material with a higher module of elasticity, e.g., a solid material like solid plastic or a metal, can be in contact with the document on the other side of the document. The one or more counter components can be configured as a transport means, e.g., a counter roller, or as a support component, e.g. a support plate. The deformable material can comprise at least one of rubber, duromer, elastomer, or thermoplast. For example, the deformable material can comprise Thermoplast® K manufactured and sold by KRAIBURG TPE GmbH & Co. KG. In particular Thermoplast® K TC5GPZ can be used. Using Thermoplast® K can have the advantage to produce the light barriers in a single two compound handling manufacturing process. Another example for a suitable material is Polyurethane.

According to another aspect of the subject matter, the one or more light barriers can have the shape of a roller and the one or more rollers can be rotatable about at least one axis. In this case, the portion of the roller that can come into contact with the document and that can comprise the deformable material can be an outer ring portion of the one or more rollers. The outer ring portion of the one or more rollers can deform when the one or more light barriers come into contact with the document. This can result in a contact area of each of the one or more rollers on the document having a length between 2 mm and 8 mm, in particular between 3 to mm and 7 mm, in particular between 4 and 6 mm. Therefore, in an example implementation and in no way limiting the scope or interpretation of the claims, not only the contact area between the one or more light barriers and the document is increased, but also the light barrier effect is enhanced. The light barrier can be arranged relative to the above described one or more counter components so that a force or pressure between these components is generated due to the deformation of the deformable material applied to either the one or more light barriers or the one or more counter components on respective sides of the document or to both of them. The pressure between the one or more light barriers and the document or rather the one or more counter components depends on the module of elasticity of the deformable material. The pressure can also be adapted by varying the durometer of the deformable material. The document can be arranged between the one or more light barriers and the one or more counter components so that the enlarged contact area of each of the one or more light barriers is induced by the force or pressure between the one or more light barriers and the one or more counter components. Alternatively or additional, a force or pressure between the one or more light barriers and the document or rather the one or more counter components can be applied by a mechanical mechanism like a resilient member, a pneumatic actuator or a hydraulic actuator. The additional mechanical mechanism can also be used to adapt the device so that the device can be used at once with a plurality of documents, e.g. a bundle of documents.

The force generated between the one or more light barriers and the document or rather the one or more counter components when one or more light barriers are in contact with the document can be a net force per light barrier of between, e.g., 0.1 N and 25 N, between 0.2 N and 10 N, in particular of between 0.5 N and 2 N. Alternatively, the force can be defined with respect to the length of the contact area per light barrier. Referred thereupon, a force between, e.g., 0.025 N/mm and 6.25 N/mm, between 0.05 N/mm and 2.5 N/mm, in particular between 0.125 N/mm and 0.5 N/mm relative to a length of the contact area of one of the one or more light barriers with the document can be generated.

In an alternative embodiment, the one or more light barriers can have the shape of to a polygon, and the one or more polygons can be rotatable about at least one axis.

For some embodiments, either equipped with rollers or polygons, the at least one axis can be movable in a direction perpendicular to the at least one axis. Further, the polygons or rollers can be mounted to a mechanical mechanism like a resilient member, a pneumatic cylinder or a hydraulic cylinder so that the polygons or rollers can rotate about at least one axis with an up and down motion remaining in contact with the document during a detection process. The mechanical mechanism can be the same mechanism as described above with respect to the force or pressure applied to the light barrier(s) and the document or rather the counter components.

According to another aspect of the subject matter, the device can further comprise one or more covers arranged about the one or more light barriers to prevent light from travelling around the light barrier.

In an alternative embodiment, the light barrier can comprise a plurality of walls arranged perpendicular to each other to form a grid of compartments. The grid can have dimensions of between 50 mm by 100 mm to 90 mm by 180 mm.

As described above in more detail in combination with the embodiment equipped with rollers, the deformable material, when applied to the contacting areas of the one or more light barriers in the shape of a polygon or to the contacting areas of the light barrier in the shape of a grid, also provides an increased area of contact between the light barriers and the document and thus an increased light barrier effect.

According to another aspect, the one or more light barriers of embodiments with the rollers or the polygons or the walls forming the grid shaped light barrier can have a width between 0.1 mm to 4 mm, in particular between 0.3 mm and 2 mm, in particular between 0.5 mm and 1 mm.

According to another aspect of the present subject matter, the one or more light sources can emit visible light, UV light and/or IR light, preferably IR light. The one or more light sources can emit light of wavelengths selected from a range of 300 nm to 2000 nm, in particular from 500 nm to 700 nm and/or from 700 nm to 2000 nm.

According to another aspect of the present subject matter, the device can further comprise a control unit comprising a storage medium encoded with a computer program and a data processing apparatus. The computer program can comprise a software or a firmware. The computer program can comprise instructions that when executed by the data processing apparatus cause the control unit to detected at least a minor amount of light emitted from the one or more light sources at the one or more light receivers although the one or more light barriers are in contact with the document. The computer program can further comprise instructions that when executed by the data processing apparatus cause the control unit to adapt an evaluation of a detected light intensity at the one or more light receivers based on characteristics of the tested document. The adaption of the detected light intensity can be based on a color composition and/or an absorption pattern of the tested document. The computer program can further comprise instructions that when executed by the data processing apparatus cause the control unit to normalize the detected light intensity based on a color composition and/or an absorption pattern of the tested document. The detected documents can comprise patterns of a plurality of different colors or of only, e.g., two main colors. The device can normalize the detected light intensity values based on the (known) composition of areas of brighter color (e.g. white areas absorbing little light) and areas of darker color (e.g. black areas, absorbing much light) on the document stored in the storage medium of the control unit. The computer program can also comprise instructions that when executed by the data processing apparatus cause the control unit to adapt a force for bringing the one or more light barriers into contact with the document. The force can be adapted by the above described mechanical mechanism. The force can be adapted based on document properties. The document properties can comprise one or more of document material, document thickness, document size and document condition. The document characteristics and/or document properties can be stored in the storage medium described above in combination with the control unit.

According to another aspect of the present subject matter, a system for detecting a tape on a document comprises at least two of the devices for detecting a tape on a document according to one of the above-described embodiments. The at least two devices can be arranged inversely on respective opposite sides of the tested documents. The at least two devices can be arranged so that, when one of the light sources of a first one of the at least two devices is positioned on a first side of the document, one of the light detectors of a second one of the at least two devices is arranged at the same position at the opposite side of the banknote. Alternatively, the at least two devices can be arranged so that when one of the light sources of a first one of the at least two devices is positioned on a first side of the document, one of the light sources of a second one of the at least two devices is arranged at the same position at the opposite side of the banknote. Alternatively, a first one of the at least two devices can be arranged at a first position on a first side of the document path and a second one of the at least two devices can be arranged at a second position on a second side of the document path. The first position and the second position can be different positions along the document path. With such an arrangement, a top side and a bottom side of the document are checked for tapes at different positions within the system.

According to another aspect of the present subject matter, a cash validator comprises a system as described above.

According to another aspect of the present subject matter, a vending machine comprises a cash validator as described above.

Another aspect of the present subject matter describes a method for detecting a tape on a document. The method can be applied to any of the above-described embodiments of the device, to the system, to the cash validator or to the vending machine. The method comprises the steps of:

First, a document is forwarded to a detection position and brought into contact with at least one light barrier. Then, light is emitted from at least one light source arranged on a first side of the light barrier. The light emitted from the at least one light source is detected at at least one light receiver arranged on a second side of to the light barrier opposite to the first side. Based on the detected light intensity at the at least one light receiver it is determined if a piece of tape is attached to the document.

A plurality of light barriers can be arranged across a width of a detection region and/or across a length of the detection region. The distance between respective of the plurality of light barriers can be between 2 mm and 15 mm, in particular between 4 mm and 8 mm, in particular between 5 mm and 7 mm.

According to another aspect of the present subject matter, the method can comprise emitting light from a plurality of light sources and receiving light at a plurality of light receivers wherein the plurality of light sources and the plurality of light receivers are arranged between the plurality of light barriers. The plurality of light barriers can be arranged to build at least three compartments and one or more of either a light source or a light receiver can be arranged per compartment. The light sources and the light receivers can be arranged alternately in consecutive compartments. In an example implementation and in no way limiting the scope or interpretation of the claims, this can be advantageous as the light from one light source can be detected by all light receivers arranged in the compartments adjacent to the compartment with the light source. Hence, in the example implementation, an easy and reliable method for detecting tapes on a document can be implemented.

As described above, at least a portion of the one or more light barriers can comprise a deformable material; in particular, a portion coming into contact with the document can comprise the deformable material to provide a tight contact and an increased area of contact between the one or more light barriers and the document during the detection.

According to another aspect of the present subject matter, the one or more light barriers can have the shape of a roller, and wherein the one or more rollers are rotatable about at least one axis. As described above, a portion coming into contact with the document and can comprise a deformable material. In case of the light barriers having the shape of a roller an outer ring portion of the one or more to rollers can comprise the deformable material. Further, the outer ring portion of the one or more rollers can deform when the one or more light barriers come into contact with the document resulting in a contact area of the one or more rollers on the document having a length between 2 mm and 8 mm, in particular between 3 mm and 7 mm, in particular between 4 and 6 mm.

According to another aspect of the present subject matter, the method can further comprise the step of applying a force to bring the one or more light barriers into contact with the document. The light barrier can be arranged relative to the above described one or more counter components so that a force or pressure between these components is generated due to the deformation of the deformable material applied to either the one or more light barriers or the one or more counter components on respective sides of the document or to both of them. The pressure between the one or more light barriers and the document or rather the one or more counter components depends on the module of elasticity/durometer of the deformable material. During the detection process, the document can be arranged between the one or more light barriers and the one or more counter components so that the enlarged contact area of each of the one or more light barriers is induced by the force or pressure between the one or more light barriers and the one or more counter components. Alternatively or additional, a force or pressure between the one or more light bathers and the document or rather the one or more counter components can be applied by a mechanical mechanism like a resilient member, a pneumatic actuator or a hydraulic actuator. The additional mechanical mechanism can also be used in an additional step of the method for adapting the device so that the device can be used at once with a plurality of documents, e.g. a bundle of documents.

According to another aspect of the present subject matter, the method can comprise emitting visible light, UV light and/or IR light, preferably IR light, and/or emitting light of wavelengths selected from a range of 300 nm to 2000 nm, in particular from 500 nm to 700 nm and/or from 700 nm to 2000 nm.

The step of detecting can comprise detecting a minor amount of light emitted to from the one or more light sources at the one or more light receivers although the one or more light barriers are in contact with the document.

According to another aspect of the present subject matter, the method can comprise the step of adapting the determining step based on characteristics of the tested document. The step of adapting the determining step can be based on a color composition and/or an absorption pattern of the tested document. The method can further comprise the step of normalizing the detected light intensity based on a color composition and/or an absorption pattern of the tested document. The adaption of the determining step can be based on the normalized light intensity values. As described in combination with the device, the detected documents can comprise patterns of a plurality of different colors or of only, e.g., two main colors. The detected light intensity values can be normalized based on the (known) composition of areas of brighter color (e.g. white areas absorbing little light) and areas of darker color (e.g. black areas, absorbing much light) on the document stored in the storage medium of the control unit. For example, prior to the process of detecting tapes on the document, the denomination and/or currency of the inserted document have been determined. The color composition of the document is stored for each denomination and/or currency in a storage medium and can now be provided for the normalization of the light intensity detected during the tape detection process.

According to another aspect of the present subject matter, the method can comprise the step of adapting a force for bringing the one or more light barriers into contact with the document. The force can be adapted based on document properties. The document properties can comprise one or more of document material, document thickness, document size, and document condition.

The method can further comprise the step of receiving information about the document characteristics and/or properties from a storage medium.

According to another aspect of the present subject matter, when the method is applied to a device having more than one light source, or a system, or a cash validator having more than one detection device arranged on one or both sides of the document, the step of emitting light from the one or more light sources can be adapted in accordance with the arrangement of the light sources. The method can be adapted so that only light sources arranged along a line parallel to the longitudinal axis or the lateral axis of the document emit light at the same time. The method can be adapted so that only light sources arranged in one compartment emit light at the same time. The method can be adapted, so that light sources arranged at the same position and on opposite sides of the document, more particular above and below the document (facing each other), do not emit light at the same time. The method can be adapted, so that light sources arranged on opposite sides of the document, more particular above and below the document, and on different sides of the light barriers (not facing each other) do not emit light at the same time.

These aspects, and how they are achieved, are explained in the detailed description in combination with the drawings.

BRIEF DESCRIPTION OF THE DRAWINGS

FIGS. 2A to 2D illustrate devices and systems for detecting a tape on a document according to embodiments of the present subject matter.

DETAILED DESCRIPTION

Figure 1:
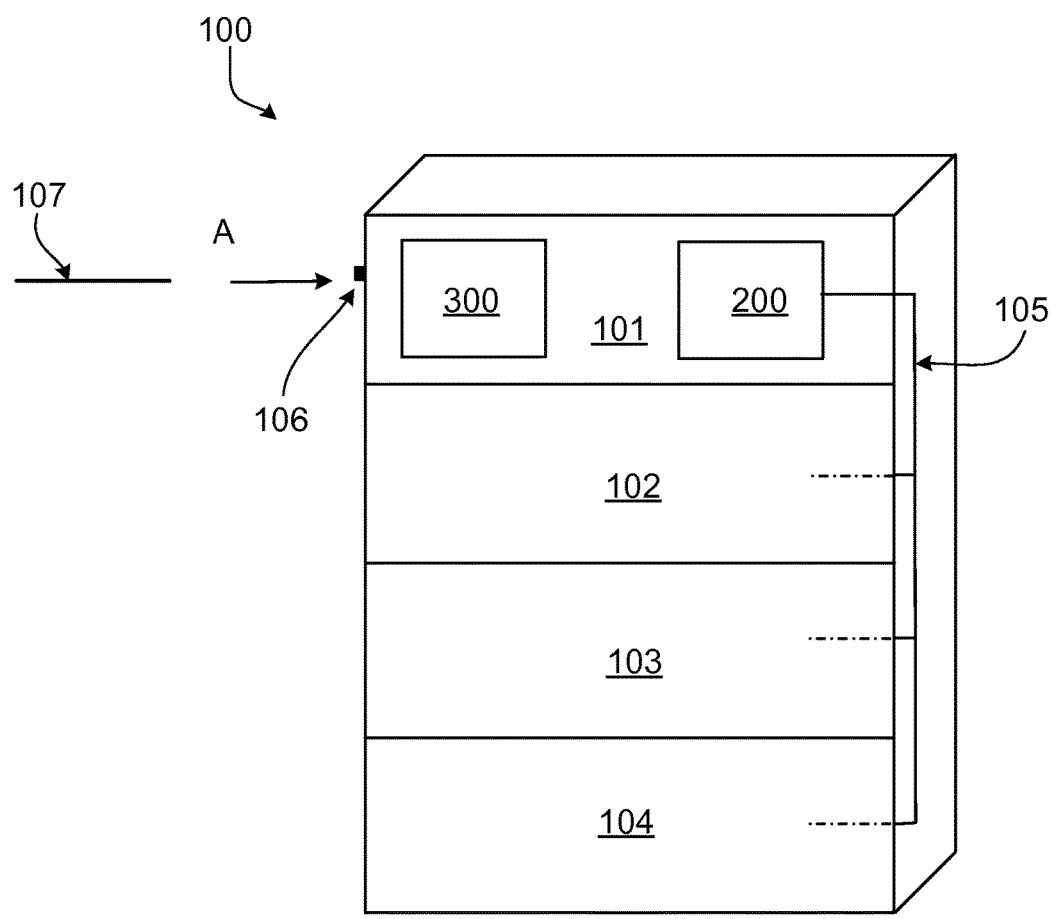
FIG. 1 illustrates a document handling apparatus, e.g., a vending machine.

FIG. 1 shows a document acceptor assembly 100, for example for the use with a vending machine. The acceptor assembly comprises a cash validator 101, a cashbox 102, a loader/dispenser 103 and at least one recycler module 104. The cash validator 101 comprises an inlet slot 106. A document 107 is inserted into the document acceptor assembly 100 via inlet/outlet slot 106 in direction of arrow A. The acceptor assembly further comprises a spine 105 that interconnects the cash validator 101, the cashbox 102, the loader/dispenser 103 and the recycler module(s) 104. The spine is designed to transport the accepted documents for storing in the acceptor assembly or for transporting documents for dispensing to the inlet/outlet 106.

The cash validator 101 comprises validation/identification unit 300 and a tape detection system 200 comprising at least two tape detection devices. The validation/identification unit 300 can be designed to determine if a genuine or counterfeit document is inserted and/or the denomination/currency of the inserted document.

FIG. 2a and FIG. 2b are sectional drawings of a tape detection system 200. FIG. 2a shows a single tape detection device of a tape detection system 200 arranged on one side of the document 107 to be detected and a counter component in form of a support plate 240 arranged on the opposite side of the document 107. FIG. 2b shows two tape detecting devices arranged in a mirrored fashion on both sides of the document 107. Respective light barriers 230 of the two devices device act as counter components for each other to clamp the document to be detected. Each device comprises at least one light source 210, at least one light receiver 220, and at least one light barrier 230. The at least one light source 210 is arranged on a first side of the at least one light barrier 230, the at least one light receiver 220 is arranged on a second side of the at least one light barrier 230 opposite to the first side. The light barrier is configured to come into contact with a document 107 to prevent or reduce light emitted from the light source 210 on the first side of the light barrier 230 to be transmitted to the light receiver 220 on the second side of the light barrier. The light source 210, the light barrier 230, and the light detector 220 of one device are arranged on the same side of the document 107.

The device can be arranged so that when a piece of tape is attached to a region of the document 107 where the light barrier 230 is in contact with the document, an amount of light is transmitted from the light source 210 through the piece of tape to the light receiver 220 on the other side of the light barrier. When a piece of tape is attached to a region of the document 107 where the light barrier 230 is in contact with the document 107 a light intensity detected by the light receiver 220, can be at least 2 times, in particular at least 5 times higher than a light intensity detected when the document 107 does not have a piece of tape attached to the region of the document 107 where the light barrier 230 is in contact with the document 107. The light intensity detected when a piece of tape is attached to the document 107 can be between 2 and 100 times, between 5 and 50 times, in particular between 10 and 25 times higher than the light intensity detected without a piece of tape attached to the document 107. The piece of tape can have a thickness between 10 µm to 200 µm, in particular between 20 µm and 100 µm, in particular between 30 µm and 60 µm. The dimensions of the piece of tape that can be detected by the device can be between 15 mm by 80 mm and 5 mm by 10 mm.

The device further comprises a document transport path and a transport means to forward the document 107 along the transport path. The document transport path and the light barrier 230 can be arranged so that the document 107, when forwarded along the document transport path by the transport means, comes into contact with the light barrier 230 when passing the light barrier 230. Examples for a transport means are a transport belt/film or transport rollers.

Figure 2C:
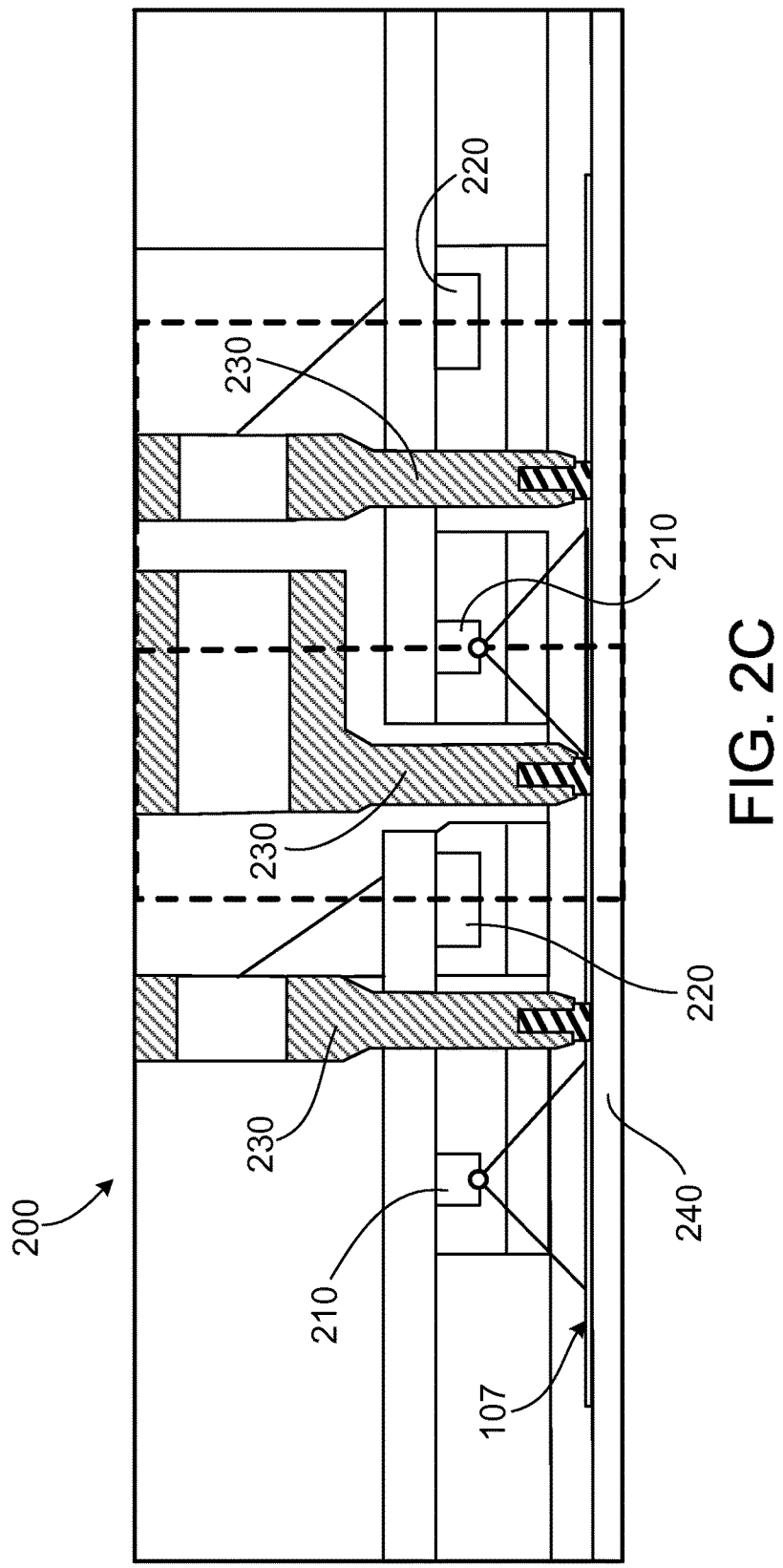
Figure 2D:
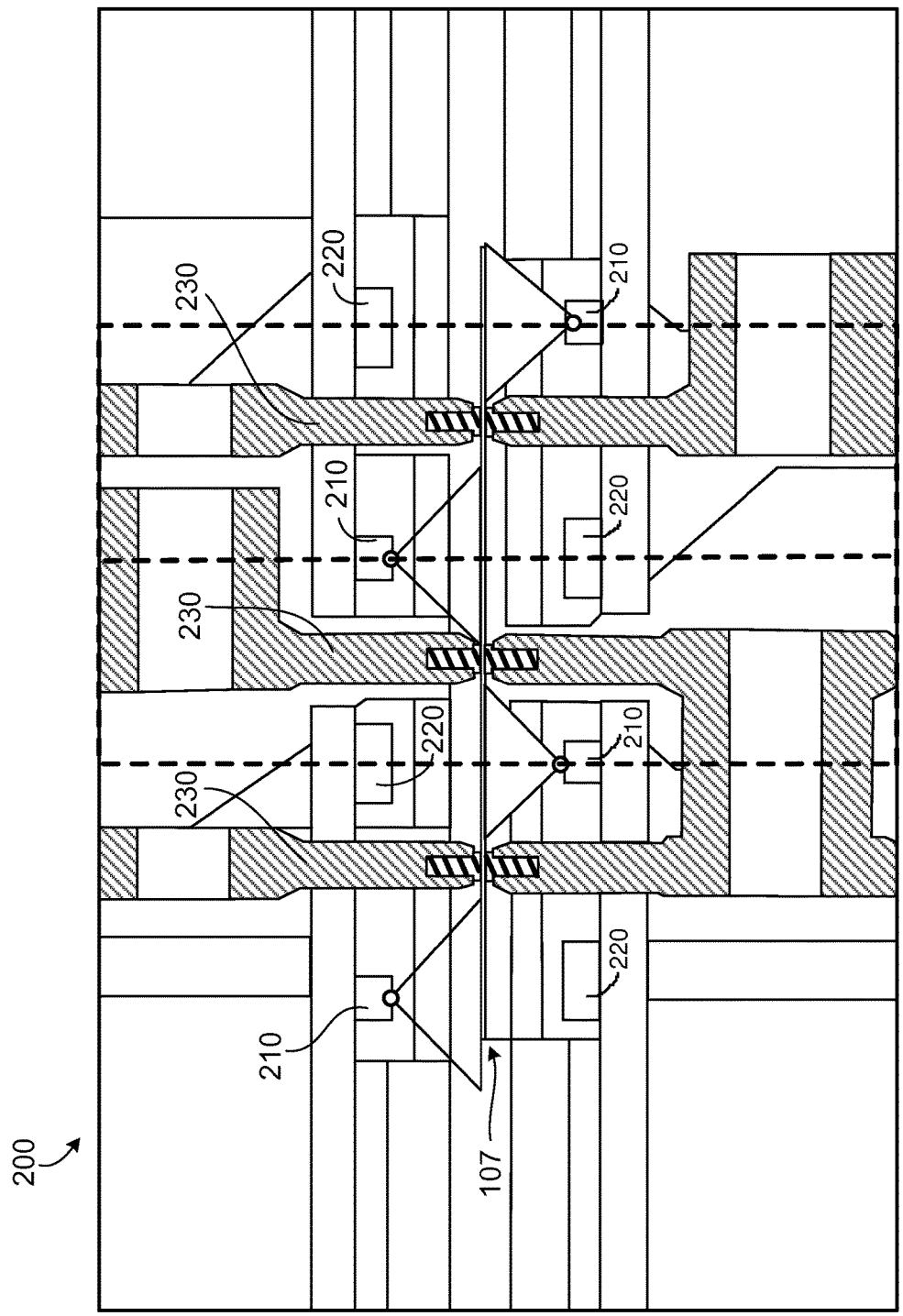

In some embodiments, as shown in FIG. 2c, a plurality of light barriers 230 are arranged across a width of a detection region and/or across a length of the detection region. The distance between respective of the plurality of light barriers 230 can be between 2 mm and 15 mm, in particular between 4 mm and 8 mm, in particular between 5 mm and 7 mm. A plurality of light sources 210 and a plurality of light receivers 220 are arranged between the plurality of light barriers 230. The plurality of light barriers 230 are arranged to build at least three compartments and one or more of either the plurality of light sources 210 or the plurality of light receivers 220 are arranged per compartment. The light sources 210 and the light receivers 220 are arranged alternately in consecutive compartments. In particular, when one or more light sources 210 are arranged in a first compartment then one or more light receivers 220 are arranged in compartments adjacent to the first compartment or when one or more light receivers 220 are arranged in the first compartment, one or more light sources 220 are arranged in the compartments adjacent to the first compartment. Thus, the to device has compartments having alternatively one or more light sources 210 or one or more light receivers 220 and there are no compartments next to each other on the same side of the document 107 that have both a light source 210 or both a light receiver 220. This is advantageous as the light from one light source 210 can be detected by all light receivers 220 arranged in the compartments adjacent to the compartment with the light source 210. Hence, in the example, a compact and efficient arrangement can be realized. FIG. 2d shows an example for system 200 with plurality of light sources 210 and light receivers 220 on both sides of the document. As shown in FIG. 2d, the light detectors 220 are arranged at the same positions as the light sources 210 on respective opposite sides of the document 107. In an alternative embodiment, the light sources 210 and light receivers 220 are arranged so that light sources 210 and light receivers 220 face each other on respective opposite sides of the document 107.

Figure 3:
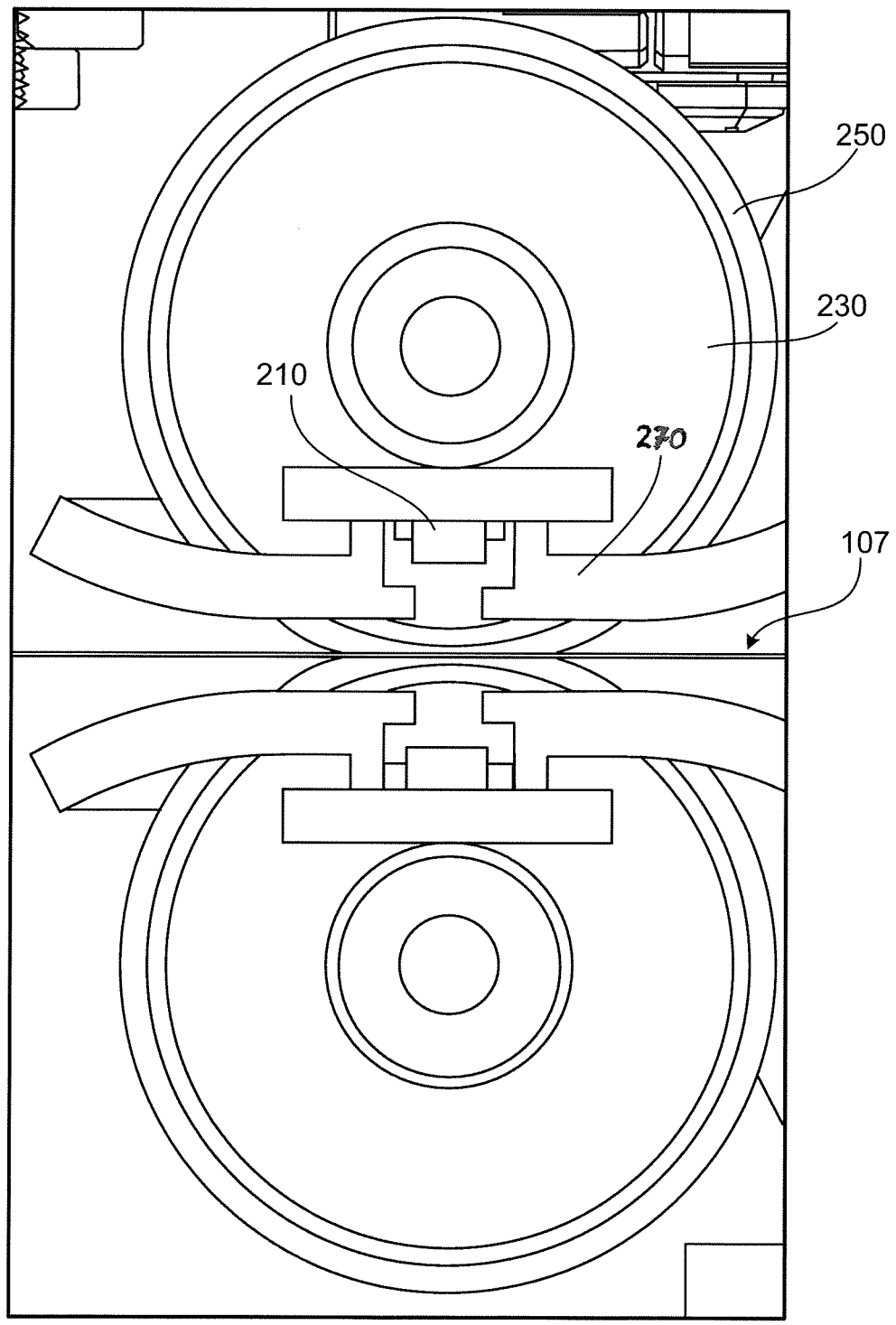
FIGS. 3 and 4 illustrate further views of the device/system according to one embodiment of the present subject matter.

At least a portion 250 of the one or more light barriers 230 comprises a deformable material, in particular, a portion 250 coming into contact with the document 107 comprises the deformable material (see FIG. 2a and FIG. 3). The remaining portion of the one or more light barriers 230 can comprise a different material with a higher module of elasticity than the portion coming into contact with the document 107. Alternatively or additional, one or more counter components (e.g. support plate 240), arranged on the opposite side of the document (see FIG. 2a, 2c), comprise a deformable material contacting the document 107 on the opposite side as the light barrier 230. The deformable material is applied to either the one or more light barriers 230 or the one or more counter components. In an alternative embodiment, the deformable material is applied to both, the one or more light barriers 230 and the one or more counter components. The deformable material is thus either in contact with the document 107 on both sides of the document 107, or the deformable material is in contact with the document 107 on one side of the document 107 and a material with a higher module of elasticity, e.g., a solid material like solid plastic or a metal, is contact with the document 107 on the other side of the document 107. The one or more counter components can be designed as a transport means, e.g., a counter roller (for example a light barrier of another device arranged opposite of the document 107, FIG. 2b, 2d), or as a support component (e.g., support plate 240). The deformable material can comprise at least one of rubber, duromer, elastomer, or thermoplast. For example, the deformable material can comprise Thermoplast® K manufactured and sold by KRAIBURG TPE GmbH & Co. KG. In particular, Thermoplast® K TC5GPZ can be used. Using Thermoplast® K can have, for example and not limiting of the scope or interpretation of the claims, the advantage to produce the light barriers in a single two compound handling manufacturing process, e.g., a molding process. Hence, in the example, the manufacturing process of the device can be simplified and the number of parts to be assembled can be reduced. Another example for a suitable material is Polyurethane, e.g., polyurethane 0-9190/MED 55 Shore A (tested according to ASTM D2240-05 (2010) "Standard Test Method for Rubber Property—Durometer Hardness;" ASTM International, West Conshohocken, Pa., 2003, DOI: 10.1520/D2240-05R10).

Figure 4:
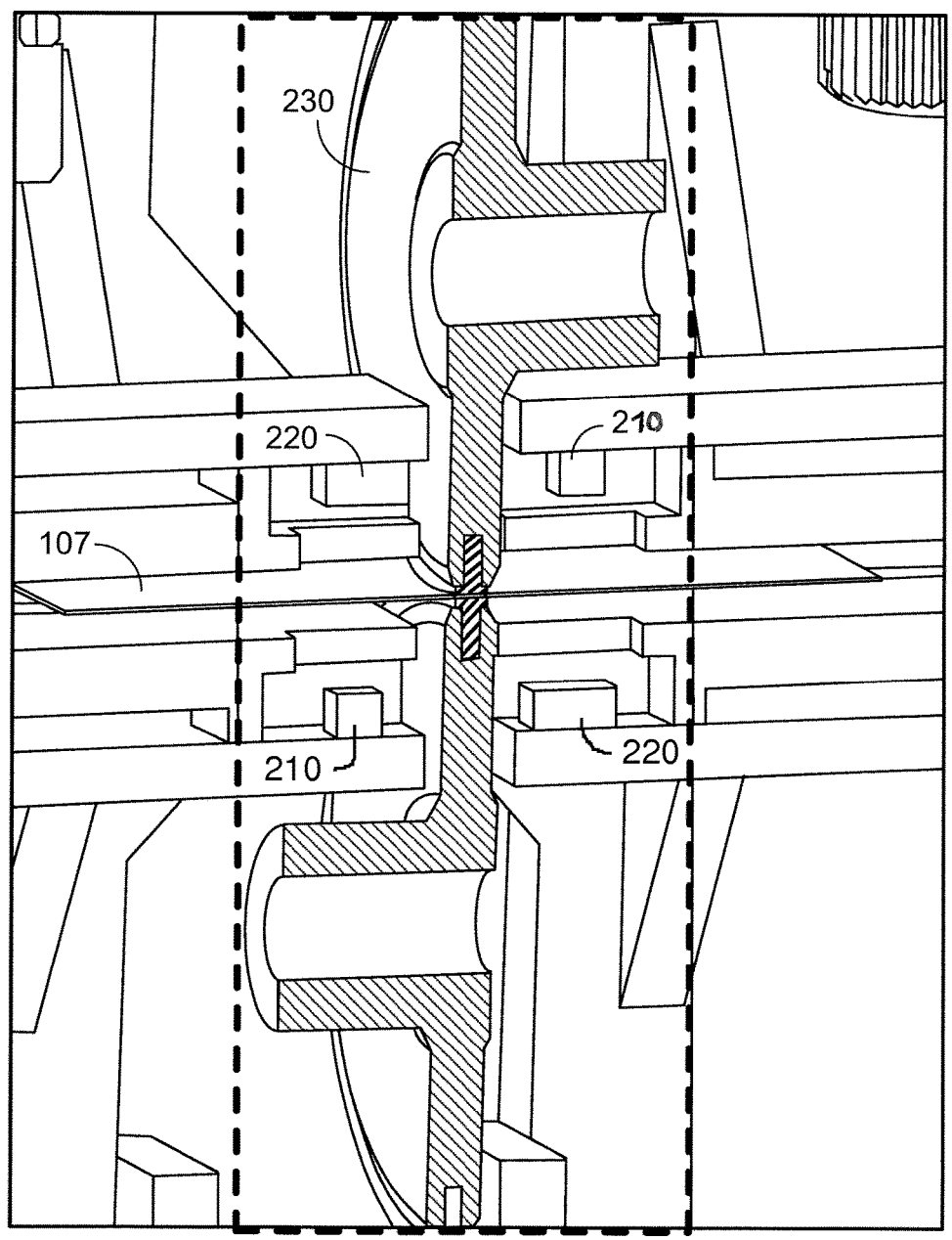

FIGS. 2 to 4 show embodiments of the present subject matter wherein the one or more light barriers 230 have the shape of a roller and the one or more rollers are rotatable about at least one axis 260 (see FIG. 2a). The portion of the roller that comes into contact with the document 107 and that comprises the deformable material can be an outer ring portion 250 of the one or more rollers (see FIG. 2a and FIG. 3). The outer ring portion 250 of the one or more rollers deforms when the one or more light barriers 230 come into contact with the document. This results in a contact area of each of the one or more rollers on the document having a length between 2 mm and 8 mm, in particular between 3 mm and 7 mm, in particular between 4 and 6 mm. Therefore, not only the contact area between the one or more light barriers 230, e.g. the rollers as shown, and the document is increased, but also the light barrier effect can be enhanced. The light barriers can be arranged relative to the one or more counter components (e.g. support plate 240) so that a force or pressure between these components is generated due to the deformation of the deformable material applied to either or both of the one or more of light barriers 230 and the one or more counter components on respective sides of the document 107. For the embodiments shown in FIG. 2a and FIG. 2c, this is achieved by having a distance between the axis of the rollers and the counter component that is less than the radius of the rollers. For the embodiment shown in FIG. 2b and FIG. 2d the distance between the axes of the rollers of to respective sides of the document is less than twice the radius of the rollers. The pressure between the one or more light barriers 230 and the document 107 or rather the one or more counter components can depend on the module of elasticity of the deformable material. The pressure can also be adapted by varying the durometer of the deformable material. As shown in FIGS. 2 to 4, the document is clamped between the one or more light barriers 230 and the one or more counter components so that the enlarged contact area of each of the one or more light barriers 230 with the document 107 is induced by the force or pressure between the one or more light bathers 230 and the one or more counter components.

Alternatively or additional, a force or pressure between the one or more light barriers 230 and the document or rather the one or more counter components is applied by a mechanical mechanism like a resilient member, a pneumatic actuator or a hydraulic actuator (not shown). The additional mechanical mechanism can also be used to adapt the device so that the device can be used at once with a plurality of documents, e.g. a bundle of documents.

The force applied between the one or more light barriers 230 and the document 107 or the counter components can be dependent on a plurality of factors. For example, the wear resistance of the deformable material can differ, the contact surface can vary, and the document 107 characteristics and condition can alter the resulting force. Generally, the force generated between the one or more light barriers 230 and the document 107 or rather the one or more counter components when one or more light barriers 230 are in contact with the document 107 can be a net force per light barrier of between, e.g., 0.1 N and 25 N, between 0.2 N and 10 N, in particular of between 0.5 N and 2 N. Alternatively, the force can be defined with respect to the length of the contact area per light barrier. Referred thereupon, a force between, e.g., 0.025 N/mm and 6.25 N/mm, between 0.05 N/mm and 2.5 N/mm, in particular between 0.125 N/mm and 0.5 N/mm relative to a length of the contact area of one of the one or more light barriers 230 with the document 107 can be generated.

Figure 5:
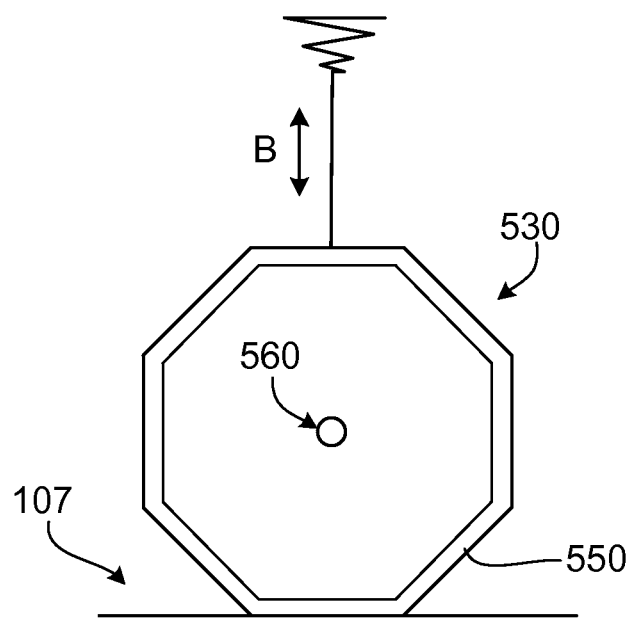
FIG. 5 illustrates an example light barrier in the form of a polygon.

In an alternative embodiment, as shown in FIG. 5, the one or more light barriers 530 have the shape of a polygon, and the one or more polygons can be rotatable to about at least one axis 560.

For both embodiments, either with rollers or polygons, the at least one axis can be movable (see arrow B in FIG. 5) in a direction perpendicular to the at least one axis 560 (260 in FIG. 2a). Further, the polygons 560 or rollers 230 can be mounted to a mechanical mechanism like a resilient member (schematically shown in FIG. 5), a pneumatic cylinder or a hydraulic cylinder so that the polygons or rollers can rotate about the at least one axis 560, 260 with an up and down motion remaining in contact with the document 107 during a detection process. The mechanical mechanism can be the same as described above with respect to the force or pressure applied to the light barriers 230 and the document 107 or rather the counter components.

In some embodiments (see FIG. 3), the device can further comprise one or more covers 270 arranged about the one or more light barriers 230 to prevent light from travelling around the light barriers 230. The covers 270 can be designed and mounted to the device so that they enclose the light sources 210 and adjoin the light barriers 230 leaving only a minimal gap between the light barriers 230 and the covers 270 so that the light emitted from the light sources 210 cannot travel around the light barriers 230 and thus cannot be wrongly detected by the light receivers 220 on the other side of the light barriers 230. The covers 270 can increase the reliability of the system, as less unwanted light may travel to and be detected by the light receivers 220 if no tape is attached to the document.

Figure 6:
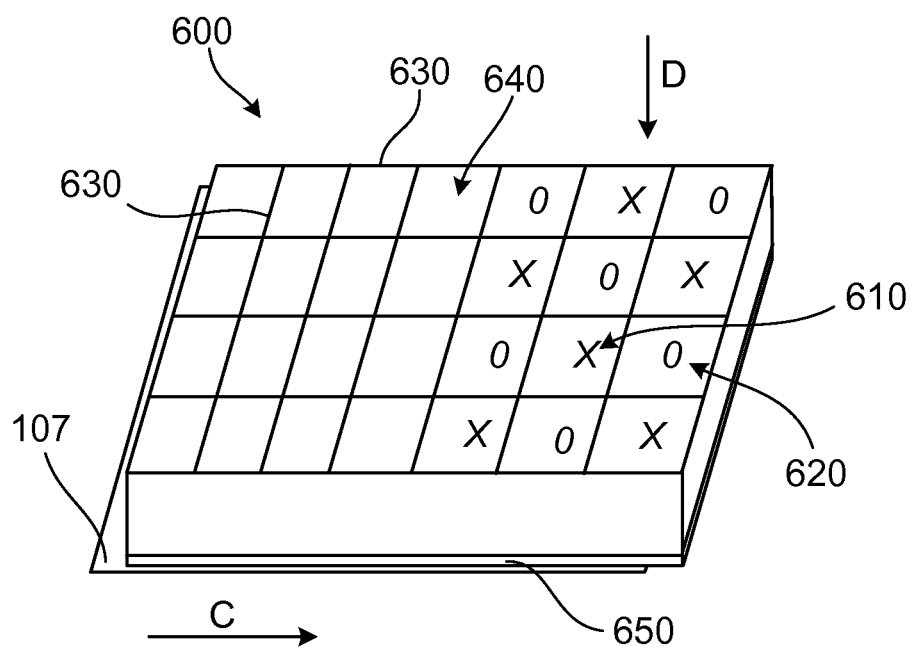
FIG. 6 illustrates an example light barrier in the form of a grid.

FIG. 6 shows the light bather 600 of an alternative embodiment. The light barrier 600 comprises a plurality of walls 630 arranged perpendicular to each other to form a grid of compartments 640. The grid has a size so that it can cover the entire document 107 that has to be checked. As the document 107 size can vary depending on the field of operation and the country of operation, the grid can have dimensions of between 50 mm by 100 mm to 90 mm by 180 mm. As shown in FIG. 6, the light sources 610 and light receivers 620 are arranged within the compartments 640 of the light barrier 600 in an alternating pattern. Therefore, the light emitted by one light source 610 can be detected by four light receivers 620 arranged in compartments 640 surrounding the compartment 640 with the light source 610. During the detection process, the document 107 is conveyed, e.g. along the document path indicated by arrow C, to a position below the grid. Then, the grid is lowered in the direction of arrow D and brought into contact with document 107. Now, the device can simultaneously detect for the entire document 107 whether a tape is attached to the document 107 by emitting light from the plurality of light sources 610 and determining if a tape guides light from a compartment with a light source 610 underneath one of the walls 630 to a compartment with a light receiver 620. As already described in more detail above, the determination if a tape is attached to the document 107 is based on the light intensity detected at the light receivers 620.

As described above in more detail in combination with the embodiment comprising rollers as light barriers, the deformable material, when applied to the contacting areas of the one or more light barriers having the shape of a polygon or to the contacting areas of the light barrier in the shape of a grid, also provides an increased area of contact between the light barrier(s) and the document and thus an increased light barrier effect. FIG. 5 shows a polygon comprising a region 550 with a deformable material. FIG. 6 shows the embodiment of the detection device with the grid defining a plurality of compartments and comprising a region 650 of a deformable material at the bottom of the plurality of walls 630 forming the grid to increase the light barrier effect.

The one or more light bathers in the shape of a roller 230 or a polygon 530 or the walls 630 forming the grid 600 have a width between 0.1 mm to 4 mm, in particular between 0.3 mm and 2 mm, in particular between 0.5 mm and 1 mm.

The one or more light sources 210, 610 can emit visible light, UV light and/or IR light. Preferably, IR light is emitted. The one or more light sources 210, 610 emit light of wavelengths selected from the range of 300 nm to 2000 nm, in particular from 500 nm to 700 nm and/or from 700 nm to 2000 nm.

In some embodiments, the device further comprises a control unit. The control unit may comprise a storage medium encoded with a computer program and a data processing apparatus. The computer program can comprise a software or a firmware. The computer program can comprise instructions that when executed by the data processing apparatus cause the control unit to detected at least a minor amount of light emitted from the one or more light sources 210, 610 at the one or more light receivers 220, 620 although the one or more light barriers are in contact with the document.

In some embodiments, the computer program further comprises instructions that when executed by the data processing apparatus cause the control unit to adapt an evaluation of a detected light intensity at the one or more light receivers 220, 620 based on characteristics of the tested document 107. The adaption of the detected light intensity can be based on a color composition and/or an absorption pattern of the tested document 107. Additionally, the computer program can comprise instructions that when executed by the data processing apparatus cause the control unit to normalize the detected light intensity based on a color composition and/or an absorption pattern of the tested document 107. The detected documents 107 can have patterns of a plurality of different colors or of only, e.g., two main colors. The device can normalize the detected light intensity values based on the (known) composition of areas of brighter color (e.g. white areas absorbing little light) and areas of darker color (e.g. black areas, absorbing much light) on the document stored in the storage medium of the control unit.

In some embodiments, the computer program comprises instructions that when executed by the data processing apparatus cause the control unit to adapt a force for bringing the one or more light barriers into contact with the document 107. The force is adapted by the above-described mechanical mechanism. The force can be adapted based on document properties. The document properties can comprise one or more of document material, document thickness, document size and document condition (creasing and dirt). The document characteristics and/or document properties can be stored for usage in the storage medium described above in combination with the control unit.

As shown in FIGS. 2b and 2d a system 200 for detecting a tape on a document comprises at least two of the devices for detecting a tape as described in detail above. The at least two devices are arranged inversely on respective opposite sides of the tested documents. The at least two devices can be arranged so that, when one of the light sources of a first one of the at least two devices is positioned on a first side of the document, one of the light detectors of a second one of the at least two devices is arranged at the same position at the opposite side of the banknote (as shown in FIG. 2d). Alternatively, the at least two devices can be arranged so that when one of the light sources of a first one of the at least two devices is positioned on a first side of the document, one of the light sources of a second one of the at least two devices is arranged at the same position at the opposite side of the banknote (not shown).

Following, a method is described for detecting a tape on a document with, e.g. a vending machine comprising an embodiment of the above-described device. For illustrative reasons, the method is described with relation to the embodiments shown in FIG. 2 to FIG. 4. However, the same method is applicable for the alternative light barrier designs shown in FIG. 5 and FIG. 6.

First, a document 107 is forwarded to a detection position and brought into contact with at least one light barrier 230. Then, light is emitted from at least one light source 210 arranged on a first side of the light barrier 230. The light emitted from the at least one light source 210 is detected at at least one light receiver 220 arranged on a second side of the light barrier 230 opposite to the first side. Based on the detected light intensity at the at least one light receiver 220 it is determined if a piece of tape is attached to the document 107.

The light intensity detected by the light receiver 220 when a piece of tape is attached to a region of the document 107 where the light barrier 230 is in contact with the document 107 can be at least 2 times, in particular at least 5 times higher than a light intensity detected when the document 107 does not have a piece of tape attached to the region of the document 107 where the light barrier 230 is in contact with the document 107. To forward the document 107 to the detection position, the document is conveyed by a transport means along a document transport path. In some embodiments, the document transport path and the light barriers 230 are arranged so that the document, when forwarded along the document transport path by the transport means comes into contact with the light barrier when passing the light barrier.

In some embodiments of the device, a plurality of light barriers 230 are arranged across a width of a detection region and/or across a length of the detection region. The distance between respective of the plurality of light barriers is between 2 mm and 15 mm, in particular between 4 mm and 8 mm, in particular between 5 mm and 7 mm.

For these embodiments, the method further comprises emitting light from a plurality of light sources 210 and receiving light at a plurality of light receivers 220 wherein the plurality of light sources 210 and the plurality of light receivers 220 are arranged between the plurality of light barriers 230. The plurality of light barriers 230 are arranged to build at least three compartments and one or more of a light source 210 or a light receiver 220 are arranged per compartment. The light sources 210 and the light receivers 220 are arranged alternately in consecutive compartments. Further details and advantages of the arrangement of the light sources 210 and light receivers 220 with respect to the light barriers 230 are described above in combination with the device.

As described above, at least a portion 250 of the one or more light bathers 230 of some of the embodiments comprises a deformable material, in particular, the portion 250 coming into contact with the document 107 comprises the deformable material to provide a tight contact and an increased contact area between the one or more light barriers 230 and the document 107 during the detection process.

In case of the light bathers 230 having the shape of a roller an outer ring portion of the one or more rollers comprise the deformable material. During the detection process, the outer ring portion of the one or more rollers deforms when the one or to more light barriers/rollers 230 come into contact with the document resulting in a contact area of the one or more rollers on the document having a length between 2 mm and 8 mm, in particular between 3 mm and 7 mm, in particular between 4 and 6 mm.

In some embodiment, the method further comprises the step of applying a force to bring the one or more light barriers into contact with the document. As described in more detail above, the light barriers 230 are arranged relative to the above-described one or more counter components so that a force or pressure between these components is generated due to the deformation of the deformable material. Alternatively or additional, a force or pressure between the one or more light barriers 230 and the document or rather the one or more counter components is applied by the above discussed mechanical mechanism.

In some embodiments, the method comprises the step of adapting the device so that the device can be used at once with a plurality of documents, e.g. a bundle of documents. The mechanical mechanism can be used for this additional step.

In some embodiments, the method comprises the step of emitting visible light, UV light and/or IR light, preferably IR light and/or emitting light of wavelengths selected from the range of 300 nm to 2000 nm, in particular from 500 nm to 700 nm and/or from 700 nm to 2000 nm.

In some embodiments, the step of detecting comprises detecting a minor amount of light emitted from the one or more light sources 210 at the one or more light receivers 220 although the one or more light barriers 230 are in contact with the document.

In some embodiments, the method further comprises the step of adapting the determining step based on characteristics of the tested document 107. The step of adapting the determining step is based on a color composition and/or an absorption pattern of the tested document 107. Additionally or alternatively, the method further comprises the step of normalizing the detected light intensity based on the color composition and/or the absorption pattern of the tested to document. The adaption of the determining step can thus be based on the normalized light intensity values. As described in combination with the device, the detected documents 107 comprise patterns of a plurality of different colors or of only, e.g., two main colors. The detected light intensity values are normalized based on the (known) composition of areas of brighter color (e.g. white areas absorbing little light) and areas of darker color (e.g. black areas, absorbing much light) on the document stored in the storage medium of the control unit. For example, prior to the process of detecting tapes on the document, the denomination and/or currency of the inserted document have been determined. The color composition of the document is stored for each denomination and/or currency in a storage medium and can now be provided for the normalization of the light intensity detected during the tape detection process.

In some embodiments, the method comprises the step of adapting a force for bringing the one or more light barriers 230 into contact with the document 107. The force may be adapted based on document properties. The document properties comprise one or more of document material, document thickness, document size and document condition.

In some embodiments, the method further comprises the step of receiving information about the document characteristics and/or properties from a storage medium.

As briefly described above, the method can also be applied to a device having more than one light source 230, or a system 200, or a cash validator 101 having more than one detection device arranged on one or both sides of the document 107. The step of emitting light from the one or more light sources 210 is adapted in accordance with the arrangement of the light sources 210. In some embodiments, the method is adapted so that only light sources 210 arranged along a line parallel to the longitudinal axis or the lateral axis of the document 107 emit light at the same time. In alternative embodiments, the method is adapted so that only light sources 210 arranged in one compartment emit light at the same time. Alternatively or additionally, the method is adapted, so that light sources arranged at the same position and on opposite sides of the document 107, more particular to above and below the document (facing each other), do not emit light at the same time. Alternatively, the method is adapted, so that light sources arranged on opposite sides of the document, more particular above and below the document, and on different sides of the light barriers (not facing each other) do not emit light at the same time.

A number of embodiments of the present subject matter have been described. Nevertheless, it will be understood that various modifications may be made without departing from the scope of the invention.

Although the present subject matter is defined in the attached claims, it is to be understood that the subject matter can alternatively also be defined in accordance with the following embodiments:

1. A device for detecting a tape on a document, the device comprising:
   at least one light source;
   at least one light receiver; and
   at least one light barrier,
   wherein the at least one light source is arranged on a first side of the at least one light barrier, the at least one light receiver is arranged on a second side of the at least one light barrier opposite to the first side, and wherein the light barrier is configured to come into contact with a document to prevent or reduce light emitted from the light source on the first side of the light barrier to be transmitted to the light receiver on the second side of the light barrier.

2. The device according to embodiment 1 wherein, when a piece of tape is attached to a region of the document where the light barrier is in contact with the document, an amount of light is transmitted from the light source through the piece of tape to the light receiver.

3. The device according to embodiment 1 or embodiment 2, wherein a light intensity detected by the light receiver, when a piece of tape is attached to a region of the document where the light barrier is in contact with the document, is at least 2 times, in particular at least 5 times higher than a light intensity detected when the document does not have a piece of tape attached to the region of the document where the light barrier is in contact with the document.

4. The device according to embodiment 2 or embodiment 3, wherein the piece of tape has a thickness between 10 μm to 200 μm, in particular between 20 μm and 100 μm, in particular between 30 μm and 60 μm.

5. The device according to anyone of the preceding embodiments further comprising a document transport path and a transport means to forward the document along the transport path.

6. The device according to embodiment 5, wherein the document transport path and the light barrier are arranged so that the document is forwarded along the document transport path by the transport means and comes into contact with the light barrier when passing the light barrier.

7. The device according to anyone of the preceding embodiments wherein a plurality of light barriers is arranged across a width of a detection region and/or across a length of the detection region.

8. The device according to embodiment 7, wherein the distance between respective of the plurality of light barriers is between 2 mm and 15 mm, in particular between 4 mm and 8 mm, in particular between 5 mm and 7 mm.

9. The device according to one of the embodiments 7 to 8, wherein a plurality of light sources and a plurality of light receivers are arranged between the plurality of light barriers.

10. The device according to embodiment 9, wherein the plurality of light barriers is arranged to build at least three compartments and wherein one or more of either the plurality of light sources or the plurality of light receivers are arranged per compartment.

11. The device according to embodiment 10, wherein the light sources and the light receivers are arranged alternately in consecutive compartments.
12. The device according to embodiment 10 or 11, wherein, when one or more light sources are arranged in a first compartment, one or more light receivers are arranged in compartments adjacent to the first compartment, and wherein, when one or more light receivers are arranged in the first compartment, one or more light sources are arranged in the compartments adjacent to the first compartment.
13. The device according to anyone of the preceding embodiments, wherein at least a portion of the one or more light barriers comprises a deformable material, in particular, wherein a portion coming into contact with the document comprises the deformable material.
14. The device according to embodiment 13, wherein a remaining portion of the one or more light barriers comprises a different material with a higher module of elasticity than the portion coming into contact with the document.
15. The device according to anyone of the preceding embodiments, wherein the one or more light barriers have the shape of a roller, and wherein the one or more rollers are rotatable about at least one axis.
16. The device according to embodiment 15 in combination with one of the embodiments 13 to 14, wherein the portion coming into contact with the document and comprising the deformable material is an outer ring portion of the one or more rollers.
17. The device according to embodiment 16, wherein the outer ring portion of the one or more rollers deforms when the one or more light barriers come into contact with the document resulting in a contact area of each of the one or more rollers on the document having a length between 2 mm and 8 mm, in particular between 3 mm and 7 mm, in particular between 4 and 6 mm.
18. The device according to one of the embodiments 1 to 14, wherein the one or more light barriers have the shape of a polygon, and wherein the one or more polygons are rotatable about at least one axis.
19. The device according to one of the embodiments 15 to 18, wherein the at least one axis is movable in a direction perpendicular to the at least one axis and wherein the polygon(s) or roller(s) is further mounted to a resilient member so that the polygon(s) or roller(s) can rotate about the at least one axis with an up and down motion remaining in contact with the document during a detection process.
20. The device according to anyone of the preceding embodiments, further comprising one or more covers arranged about the one or more light bathers to prevent light from travelling around the light barrier.
21. The device according one of the embodiments 1 to 14, wherein the light barrier comprises a plurality of walls arranged perpendicular to each other to form a grid of compartments.
22. The device according to embodiment 21, wherein the grid has dimensions of between 50 mm by 100 mm to 90 mm by 180 mm.
23. The device according to anyone of the preceding embodiments wherein the one or more light barriers have a width between 0.1 mm to 4 mm, in particular between 0.3 mm and 2 mm, in particular between 0.5 mm and 1 mm.
24. The device according to anyone of the preceding embodiments wherein a force or a pressure is generated between the one or more light barriers and the document when the light barriers are brought into contact with the document.
25. The device according to anyone of the preceding embodiments wherein the light bather is pressed on the document when brought into contact with the document with a net force per light bather of between 0.1 N and 25 N, between 0.2 N and 10 N, in particular of between 0.5 N and 2 N.
26. The device according to anyone of the preceding embodiments wherein the light bather is pressed on the document when brought into contact with the document with a force between 0.025 N/mm and 6.25 N/mm, between 0.05 N/mm and 2.5 N/mm, in particular between 0.125 N/mm and 0.5 N/mm relative to a length of the contact area of one of the one or more light bathers with the document.
27. The device according to anyone of the preceding embodiments wherein the one or more light sources emit visible light, UV light and/or IR light, preferably IR light.
28. The device according to anyone of the preceding embodiments wherein the one or more light sources emit light of wavelengths in a range from 300 nm to 2000 nm, in particular from 500 nm to 700 nm and/or from 700 nm to 2000 nm.
29. The device according to anyone of the preceding embodiments further comprising a control unit comprising a storage medium encoded with a computer program and a data processing apparatus.
30. The device according to embodiment 29, wherein the computer program comprises a software or a firmware.
31. The device according to embodiment 29 or embodiment 30, wherein the computer program comprises instructions that when executed by the data processing apparatus cause the control unit to detected at least a minor amount of light emitted from the one or more light sources at the one or more light receivers although the one or more light barriers are in contact with the document.
32. The device according to one of the embodiments 29 to 31, wherein the computer program comprises instructions that when executed by the data processing apparatus cause the control unit to adapt an evaluation of a detected light intensity at the one or more light receivers based on characteristics of the tested document.
33. The device according to embodiment 32, wherein the adaption of the detected light intensity is based on a color composition and/or an absorption pattern of the tested document.
34. The device according to embodiment 32, wherein the computer program comprises instructions that when executed by the data processing apparatus cause the control unit to normalize the detected light intensity based on a color composition and/or an absorption pattern of the tested document.
35. The device according to one of the embodiments 30 to 34, wherein the computer program comprises instructions that when executed by the data processing apparatus cause the control unit to adapt a force for bringing the one or more light bathers into contact with the document.
36. The device according to embodiment 35, wherein the force is adapted based on document properties.
37. The device according to embodiment 36, wherein the document properties comprise one or more of document material, document thickness, document size and document condition.

38. The device according one of the embodiments 32 to 37, wherein the document characteristics and/or document properties are stored in the storage medium.
39. A system for detecting a tape on a document, the system comprising at least two devices for detecting a tape on a document according to one of the preceding embodiments.
40. The system according to embodiment 39, wherein the at least two devices are arranged inversely on respective opposite sides of the tested documents at same positions along the document path.
41. The system according to embodiment 39 or 40, wherein the at least two devices are arranged so that when one of the light sources of a first one of the at least two devices is positioned on a first side of the document, one of the light detectors of a second one of the at least two devices is arranged at the same position at the opposite side of the banknote.
42. The system according to embodiment 39 or 40, wherein the at least two devices are arranged so that when one of the light sources of a first one of the at least two devices is positioned on a first side of the document, one of the light sources of a second one of the at least two devices is arranged at the same position at the opposite side of the banknote.
43. The system according to embodiment 39, wherein the at least two devices are arranged inversely on respective opposite sides of the tested documents at different positions along the document path.
44. A cash validator comprising at least one device according to one of the embodiments 1 to 38 or a system according to one of the embodiments 39 to 43.
45. A vending machine comprising a cash validator according to embodiment 44.
46. A method for detecting a tape on a document comprising the steps of:
    forwarding the document to a detection position and bringing at least one light barrier into contact with the document;
    emitting light from at least one light source arranged on a first side of the light barrier;
    detecting the light emitted from the at least one light source at at least one light receiver arranged on a second side of the light barrier opposite to the first side;
    determining based on the detected light intensity at the at least one light receiver if a piece of tape is attached to the document.
47. The method according to embodiment 46, wherein a light intensity detected by the light receiver, when a piece of tape is attached to a region of the document where the light barrier is in contact with the document, is at least 2 times, in particular at least 5 times higher than a light intensity detected when the document does not have a piece of tape attached to the region of the document where the light barrier is in contact with the document.
48. The method according to embodiment 46 or embodiment 47 wherein the document is forwarded by a transport means along a document transport path.
49. The method according to anyone of the embodiments 46 to 48, wherein a plurality of light barriers is arranged across a width of a detection region and/or across a length of the detection region.
50. The method according to embodiment 49, wherein the distance between respective of the plurality of light barriers is between 2 mm and 15 mm, in particular between 4 mm and 8 mm, in particular between 5 mm and 7 mm.
51. The method according to embodiment 49 or embodiment 50, further comprising emitting light from a plurality of light sources and receiving light at a plurality of light receivers wherein the plurality of light sources and the plurality of light receivers are arranged between the plurality of light barriers.
52. The method according to anyone of the preceding embodiments, wherein at least a portion of the one or more light barriers comprises a deformable material, in particular, wherein a portion coming into contact with the document comprises the deformable material.
53. The method according to embodiment 52, wherein a remaining portion of the one or more light barriers comprises a different material with a higher module of elasticity than the portion coming into contact with the document.
54. The method according to anyone of the preceding embodiments, wherein the one or more light barriers have the shape of a roller, and wherein the one or more rollers are rotatable about at least one axis.
55. The method according to embodiment 54 in combination with one of the embodiments 52 to 53, wherein the portion coming into contact with the document and comprising the deformable material is an outer ring portion of the one or more rollers.
56. The method according to embodiment 55, wherein the outer ring portion of the one or more rollers deforms when the one or more light barriers come into contact with the document resulting in a contact area of the one or more rollers on the document having a length between 2 mm and 8 mm, in particular between 3 mm and 7 mm, in particular between 4 and 6 mm.
57. The method according to one of the embodiments 46 to 53, wherein the one or more light barriers have the shape of a polygon, and wherein the one or more polygons are rotatable about at least one axis.
58. The method according to one of the embodiments 54 to 57, wherein the at least one axis is movable in a direction perpendicular to the at least one axis and wherein the polygon or roller is further mounted to a resilient member so that the polygon or roller can rotate about the at least one axis with an up and down motion remaining in contact with the document during a detection process.
59. The method according to anyone of the preceding embodiments wherein the one or more light bathers have a width between 0.1 mm to 4 mm, in particular between 0.3 mm and 2 mm, in particular between 0.5 mm and 1 mm.
60. The method according to anyone of the preceding embodiments further comprising the step of applying a force to bring the one or more light bathers into contact with the document.
61. The method according to anyone of the preceding embodiments wherein the one or more light sources emit visible light, UV light and/or IR light, preferably IR light.
62. The method according to anyone of the preceding embodiments wherein the one or more light sources emit light of wavelengths in a range from 300 nm to 2000 nm, in particular from 500 nm to 700 nm and/or from 700 nm to 2000 nm.
63. The method according to anyone of the preceding embodiments, wherein the step of detecting comprises detecting a minor amount of light emitted from the one or more light sources at the one or more light receivers although the one or more light barriers are in contact with the document.

64. The method according to anyone of the preceding embodiments, further comprising the step of adapting the determining step based on characteristics of the tested document.

65. The method according to embodiment 64, wherein adapting the determining step is based on a color composition and/or an absorption pattern of the tested document.

66. The method according to embodiment 64 or embodiment 65, further comprising the step of normalizing the detected light intensity based on a color composition and/or an absorption pattern of the tested document.

67. The method according to anyone of the preceding embodiments, further comprising the step of adapting a force for bringing the one or more light bathers into contact with the document.

68. The method according to embodiment 67, wherein the force is adapted based on document properties.

69. The method according to embodiment 68, wherein the document properties comprise one or more of document material, document thickness, document size and document condition.

70. The method according to one of the embodiments 64 to 69, further comprising the step of receiving information about the document characteristics and/or properties from a storage medium.

What is claimed is:

1. A device for detecting a tape on a document, the device comprising:
    at least one light barrier comprising a first side opposite a second side;
    at least one light source, wherein one of the at least one light source is arranged on the first side of one of the at least one light barrier;
    at least one light receiver, wherein one of the at least one light receiver is arranged on the second side of the one light barrier opposite to the first side,
    wherein the one light barrier is configured to contact a document to prevent or reduce light that is emitted from the one light source on the first side of the one light barrier to be transmitted to the one light receiver on the second side of the one light barrier, and
    wherein the one light barrier, the one light source, and the one light receiver are on a same side of the document, and
    a control unit comprising a non-transitory storage medium encoded with a computer program and a data processing apparatus,
    wherein the computer program comprises instructions that when executed by the data processing apparatus cause the control unit to detect whether the tape is on the document based on an evaluation of a detected light intensity at the one light receiver.

2. The device according to claim 1, wherein a light intensity detected by the one light receiver, when a piece of tape is attached to a region of the document where the one light barrier is in contact with the document, is at least two times higher than a light intensity detected when the document does not have a piece of tape attached to the region of the document where the one light barrier is in contact with the document.

3. The device according to claim 1, wherein the at least one light barrier comprises a plurality of light barriers arranged across a width of a detection region or across a length of the detection region, and wherein each of a plurality of light sources of the at least one light source and each of a plurality of light receivers of the at least one light receiver are arranged on opposite sides of each of the plurality of light barriers.

4. The device according to claim 1, wherein at least a portion of the at least one light barrier comprises a deformable material configured to contact the document.

5. The device according to claim 1, wherein the at least one light barrier comprises a shape of a roller to form at least one roller, and wherein the at least one roller is rotatable about at least one axis.

6. The device according to claim 5, wherein at least a portion of the at least one light barrier comprises a deformable material configured to contact the document, and wherein the deformable material is an outer ring portion of the at least one roller.

7. The device according to one of the claim 6, wherein the at least one roller is movable in a direction perpendicular to the at least one axis, and wherein the at least one roller is mounted to a resilient member so that the at least one roller can rotate about the at least one axis with an up and down motion and remaining in contact with the document during a detection process.

8. The device according to claim 1, further comprising one or more covers arranged about the at least one light barrier to prevent light from travelling around the at least one light barrier.

9. The device according to claim 1, further comprising:
    the control unit comprising the non-transitory storage medium encoded with the computer program and the data processing apparatus,
    wherein the computer program comprises instructions that when executed by the data processing apparatus cause the control unit to adapt an evaluation of a detected light intensity at the one or more light receivers based on characteristics of the document, and
    wherein the control unit is caused to normalize the detected light intensity based on a color composition or an absorption pattern of the document.

10. The device according to claim 1, wherein a light source of the at least one light source is on an opposite side of the document from a light receiver of the at least one light receiver.

11. The device according to claim 1, wherein the at least one light source, the at least one barrier, and the at least one light receiver form a grid that covers an entirety of the document.

12. The device according to claim 1, wherein the one light receiver only receives light that travels through the tape.

13. A system for detecting a tape on a document, the system comprising:
    at least two devices for detecting the tape on the document, each of the at least two devices comprising:
    at least one light barrier comprising a first side opposite a second side;
    at least one light source, wherein one of the at least one light source is arranged on the first side of one of the at least one light barrier;
    at least one light receiver, wherein one of the at least one light receiver is arranged on the second side of the one light barrier opposite to the first side, and
    wherein the one light barrier is configured to contact a document to prevent or reduce light that is emitted from the one light source on the first side of the one light barrier to be transmitted to the one light receiver on the second side of the one light barrier, and wherein the one light barrier, the one light source, and the one light receiver are on a same side of the document, and a control unit comprising a non-transitory storage medium encoded with a computer program and a data processing apparatus, wherein the computer program comprises instructions that when executed by the data processing apparatus cause the control unit to detect whether the tape is on the document based on an evaluation of a detected light intensity at the one light receiver.

14. The system according to claim 13, wherein a first device of the at least two devices is arranged inversely on an opposite side of the document at same positions along a document path.

15. The system according to claim 14, wherein the at least two devices are arranged such that each of the at least one light source of the first device positioned on a first side of the document is arranged at a same position opposite of each of the at least one light receiver of a second device of the at least two devices on a second side of the document.

16. The system according to claim 14, wherein the at least two devices are arranged such that each of the at least one light source of the first device positioned on a first side of the document is arranged at a same position opposite of each of the at least one light source of a second device of the at least two devices on a second side of the document.

17. The system according to claim 13, wherein a light intensity detected by the one light receiver, when a piece of tape is attached to a region of the document where the one light barrier is in contact with the document, is at least two times higher than a light intensity detected when the document does not have a piece of tape attached to the region of the document where the one light barrier is in contact with the document.

18. The system according to claim 13, wherein the at least one light barrier comprises a plurality of light barriers arranged across a width of a detection region or across a length of the detection region, and wherein each of a plurality of light sources of the at least one light source and each of a plurality of light receivers of the at least one light receiver are arranged on opposite sides of each of the plurality of light barriers.

19. The system according to claim 13, wherein at least a portion of the at least one light barrier comprises a deformable material configured to contact the document.

20. The system according to claim 13, wherein the at least one light barrier comprises a shape of a roller to form at least one roller, and wherein the at least one roller is rotatable about at least one axis.

21. The system according to claim 20, wherein at least a portion of the at least one light barrier comprises a deformable material configured to contact the document, and wherein the deformable material is an outer ring portion of the at least one roller.

22. The system according to one of the claim 21, wherein the at least one roller is movable in a direction perpendicular to the at least one axis, and wherein the at least one roller is mounted to a resilient member so that the at least one roller can rotate about the at least one axis with an up and down motion and remaining in contact with the document during a detection process.

23. A method for detecting a tape on a document, the method comprising:

forwarding the document to a detection position and bringing at least one light barrier into contact with the document;

emitting light from at least one light source arranged on a first side of the light barrier;

detecting the light emitted from the at least one light source by at least one light receiver arranged on a second side of the light barrier that is opposite to the first side, wherein the light barrier is directly between the at least one light source and the at least one light receiver; and determining, based on a detected light intensity at the at least one light receiver, if a piece of tape is attached to the document.

\* \* \* \* \*